(12) United States Patent
Franco et al.

(10) Patent No.: US 10,998,467 B2
(45) Date of Patent: *May 4, 2021

(54) COMPOSITIONS OF METAL OXIDE SEMICONDUCTOR NANOMATERIALS AND HEMOSTATIC POLYMERS

(71) Applicant: Nano Sono Cooperation Ltd., Upper Yokneam (IL)

(72) Inventors: Ariel Antonio Franco, Yokneam (IL); Ronen Sarusi, Yokneam (IL)

(73) Assignee: NANO SONO COOPERATION LTD., Upper Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/892,493

(22) Filed: Jun. 4, 2020

(65) Prior Publication Data

US 2021/0091266 A1 Mar. 25, 2021

Related U.S. Application Data

(63) Continuation-in-part of application No. 16/582,529, filed on Sep. 25, 2019.

(51) Int. Cl.
*H01L 33/28* (2010.01)
*C01G 3/00* (2006.01)
(Continued)

(52) U.S. Cl.
CPC ............ *H01L 33/285* (2013.01); *A61L 15/32* (2013.01); *A61L 15/44* (2013.01); *C01G 3/006* (2013.01); *C01G 3/02* (2013.01); *C01G 9/02* (2013.01); *H01L 33/0008* (2013.01); *H01L 33/06* (2013.01); *H01L 33/44* (2013.01);
(Continued)

(58) Field of Classification Search
CPC ....... H01L 33/285; H01L 33/06; H01L 33/44; H01L 33/0008; H01L 2933/0025; A61L 15/44; A61L 15/32; A61L 2300/102; A61L 2400/12; A61L 2400/04; C01G 9/02; C01G 3/02; C01G 3/006; B82Y 20/00; B82Y 40/00; B82Y 30/00; C01P 2002/72; C01P 2006/40; C01P 2002/82; C01P 2002/01
See application file for complete search history.

(56) References Cited

U.S. PATENT DOCUMENTS 7,998,504 B2   8/2011  Djokic
8,425,880 B1   4/2013  Lyczak et al.
(Continued)

FOREIGN PATENT DOCUMENTS

WO   2002039963 A1   5/2002
WO   2003080231 A1   3/2004
(Continued)

OTHER PUBLICATIONS

Carbone, et al., Antimicrobial power of Cu/Zn mixed oxide nanoparticles to *Escherichia coli*, Environmental Nanotechnology, Monitoring & Management 2017; 7: 97-102 (Year: 2017).*
(Continued)

*Primary Examiner* — Daniel C. McCracken
(74) *Attorney, Agent, or Firm* — Polsinelli PC

(57) ABSTRACT

The present invention provides composition comprising a metal oxide semiconductor nanomaterial coated or dispersed with a hemostatic polymer.

9 Claims, 7 Drawing Sheets

$$5(Cu_{1-x}Zn_x)(CH_3COO^-)_2 + 10NH_4HCO_3 \xrightarrow[-6H_3O^+]{H_2O, rT} (Cu_{1-x}Zn_x)_5(OH)_6(CO_3)_2 + 10NH_4CH_3COO + 8CO_2$$

$$(Cu_{1-x}Zn_x)_5(OH)_6(CO_3)_2 \xrightarrow[-3H_2O]{200°C} (Cu_{1-x}Zn_x)_5O_3(CO_3)_2 (yellow)$$

$$(Cu_{1-x}Zn_x)_5O_3(CO_3)_2 \xrightarrow[-2CO_2]{300°C} 5Cu_{1-x}Zn_xO (brown)$$

(51) Int. Cl.
| | |
|---|---|
| A61L 15/32 | (2006.01) |
| A61L 15/44 | (2006.01) |
| C01G 9/02 | (2006.01) |
| H01L 33/00 | (2010.01) |
| H01L 33/06 | (2010.01) |
| H01L 33/44 | (2010.01) |
| C01G 3/02 | (2006.01) |
| B82Y 20/00 | (2011.01) |
| B82Y 30/00 | (2011.01) |
| B82Y 40/00 | (2011.01) |

(52) U.S. Cl.
CPC ..... *A61L 2300/102* (2013.01); *A61L 2400/04* (2013.01); *A61L 2400/12* (2013.01); *B82Y 20/00* (2013.01); *B82Y 30/00* (2013.01); *B82Y 40/00* (2013.01); *C01P 2002/01* (2013.01); *C01P 2002/72* (2013.01); *C01P 2002/82* (2013.01); *C01P 2006/40* (2013.01); *H01L 2933/0025* (2013.01)

(56) References Cited

U.S. PATENT DOCUMENTS

| | | |
|---|---|---|
| 2003/0185889 A1 | 10/2003 | Yan et al. |
| 2007/0275101 A1* | 11/2007 | Lu ..................... A61L 2/232 424/719 |
| 2008/0085326 A1 | 4/2008 | Ruan |
| 2008/0317830 A1 | 12/2008 | Goldstein et al. |
| 2013/0168328 A1 | 7/2013 | Bagabas et al. |
| 2013/0315972 A1 | 11/2013 | Krasnow et al. |
| 2014/0017462 A1 | 1/2014 | Borrelli et al. |
| 2014/0276322 A1 | 9/2014 | Murphy et al. |
| 2015/0196066 A1 | 7/2015 | Emanuel et al. |
| 2016/0250612 A1 | 9/2016 | Oldenburg et al. |
| 2017/0252440 A1 | 9/2017 | Wu et al. |
| 2018/0036426 A1 | 2/2018 | Rajh et al. |
| 2020/0100503 A1 | 4/2020 | Kanovsky |

FOREIGN PATENT DOCUMENTS

| | | |
|---|---|---|
| WO | 2004101014 A2 | 7/2005 |
| WO | 2006048879 A1 | 5/2006 |
| WO | 2007147842 A2 | 3/2008 |
| WO | 2018099945 A1 | 6/2018 |
| WO | 2020041472 A1 | 2/2020 |

OTHER PUBLICATIONS

Periodic Table Atomic Properties of the Elemetns, NIST SP 966 (Sep. 2010) (Year: 2010).*
Wang, et al., Reduced graphene oxide decorated with CuO—ZnO hetero-junctions: towards high selective gas-sensing property to acetone, J. Mater. Chem. A 2014; 2: 18635-18643 (Year: 2014).*
Brady, et al., Mineral Formulae Recalculation, accessed online at https://serc.carleton.edu/research_education/equilibria/mineralformulaerecalculation.html on Dec. 22, 2020 (hereinafter "Brady at_") (Year: 2020).*
Assal, et al.; "Synthesis, Characterization, and Relative Study on the Catalystic Activity of Zinc Oxide Nanoparticles doped MnCO3, MnO2, Mn2O3 for Ariel Oxidation of Alcohols", Journal of chemistry, 2017 (Jul. 12, 2017).
International Search Report of PCT/US20/13793, dated Mar. 19, 2020.
Tamanis, et al., "Synthesis of Core/Shell CuO—Zno Nanoparticles and Their Second-Harmonic Generation Performance" Latvian Journal of Physics and Technical Sciences 52.5 (Oct. 1, 2015): 41-46. Abstract, p. 41 para 2; p. 43 para 2; p. 44 para 3; Figure 2.
Wang, et al. "Reduced graphene oxide decorated with CuO—ZnO hetero-junctions: towards high selective gas-sensing property to acetone." Journal of Materials Chemistry A 2.43 (Sep. 19, 2014): 18635-18643. Abstract, p. 1 col. 2 para 1; p. 3 col. 2 para 2; p. 5 col. 2 para 1.
Carbone, et al. "Antimicrobial power of Cu/Zn mixed oxide nanoparticles to *Escherichia coli*." Environmental Nanotechnology, Monitoring & Management 7 (May 1, 2017): 97-102. Abstract, Table 2.
Kozhushner, et al. "Inhomogeneous charge distribution in semiconductor nanoparticles." The Journal of Physical Chemistry C 119.28 (Jul. 16, 2015): 16286-16292. Abstract, p. 16286 col. 2 para 2—p. 16287 col. 1 para 1; p. 16291 col. 2 para 4.
Vaseem, et al. "Copper oxide quantum dot ink for inkjet-driven digitally controlled high mobility field effect transistors." Journal of Materials Chemistry C 1.11 (Jan. 24, 2013): 2112-2120. Abstract.
Lin, et al. "Band gap variation of size-controlled ZnO quantum dots synthesized by sol-gel method." Chemical Physics Letters 409.4-6 (Jun. 30, 2005): 208-211. Abstract, p. 209 col. 1 para 4; Figure 1; and Figure 4.

* cited by examiner

US 10,998,467 B2

COMPOSITIONS OF METAL OXIDE SEMICONDUCTOR NANOMATERIALS AND HEMOSTATIC POLYMERS

CROSS REFERENCE TO RELATED APPLICATIONS

This application is a continuation-in-part of U.S. application Ser. No. 16/582,529, filed on Sep. 25, 2019 which is hereby incorporated by reference in their entirety.

FIELD OF THE INVENTION

The present disclosure generally relates to hemostatic polymers coated or adhered on metal oxide semiconductor nanomaterials.

BACKGROUND OF THE INVENTION

Metal oxide semiconductor nanomaterials and especially copper oxide (CuO) and zinc oxide (ZnO) nanomaterials ($Cu_{1-x}/Zn_xO$) have been previously reported possessing antibacterial, antimicrobial, and antifungal properties. Hemostatic polymers are widely known to coagulate blood through various mechanisms. Coating or adhering a hemostatic polymer onto the surface of the metal oxide semiconductor nanomaterial would provide not only antibacterial, antimicrobial, and antifungal properties but also provide coagulation properties.

What is needed are improved compositions comprising metal oxide semiconductor nanomaterials which exhibit many beneficial properties which are coated or adhered to a hemostatic polymer to provide additional coagulation properties.

SUMMARY OF THE INVENTION

Figure 1:
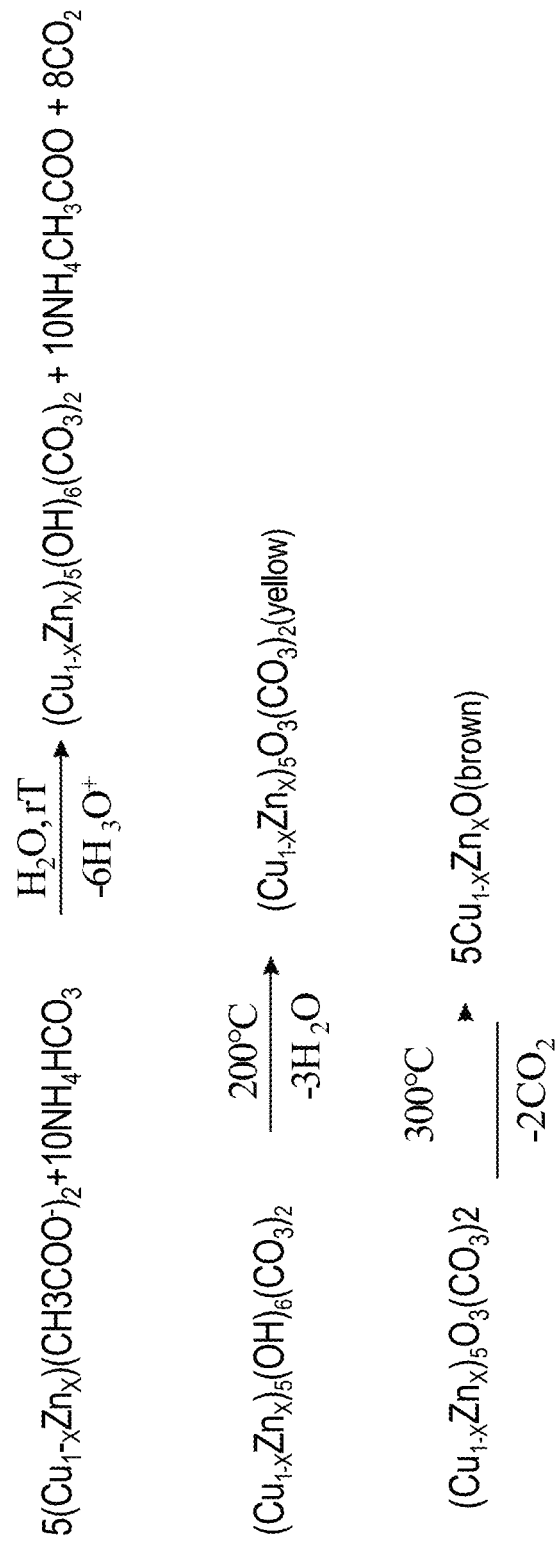
FIG. 1 is a chemical scheme for the nanoparticle preparation. The scheme demonstrates preparation and precipitation of Aurichalcite precursor in the first step; the dehydration of the Aurichalcite precursor in step 2; and thermal decomposition of the Aurichalcite precursor to metal oxide to form the metal oxide semiconductor nanomaterials in step 3.
Figure 2:
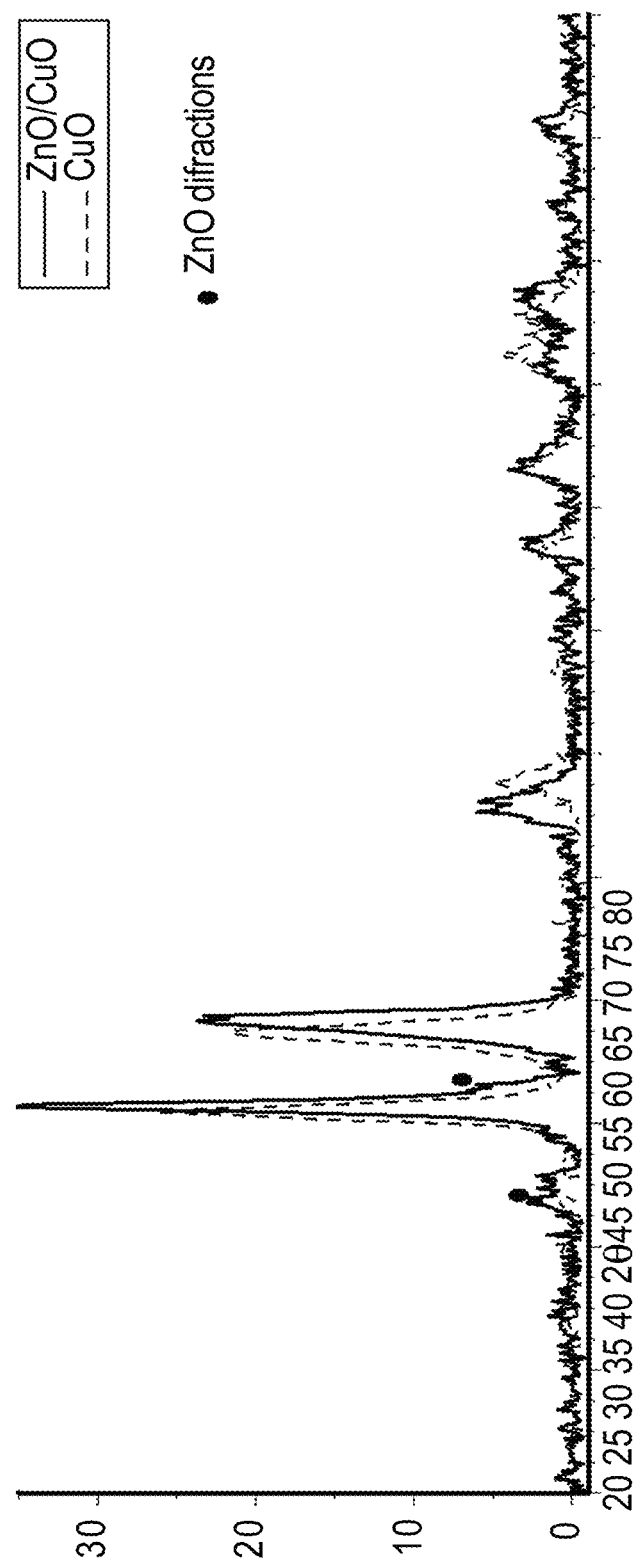
FIG. 2 is a comparison of the XRD diffractograms for pure CuO and $CuO_{1-x}/ZnO_x$. The diffractograms show the shift for some diffraction signals related to ZnO faces.
Figure 3:
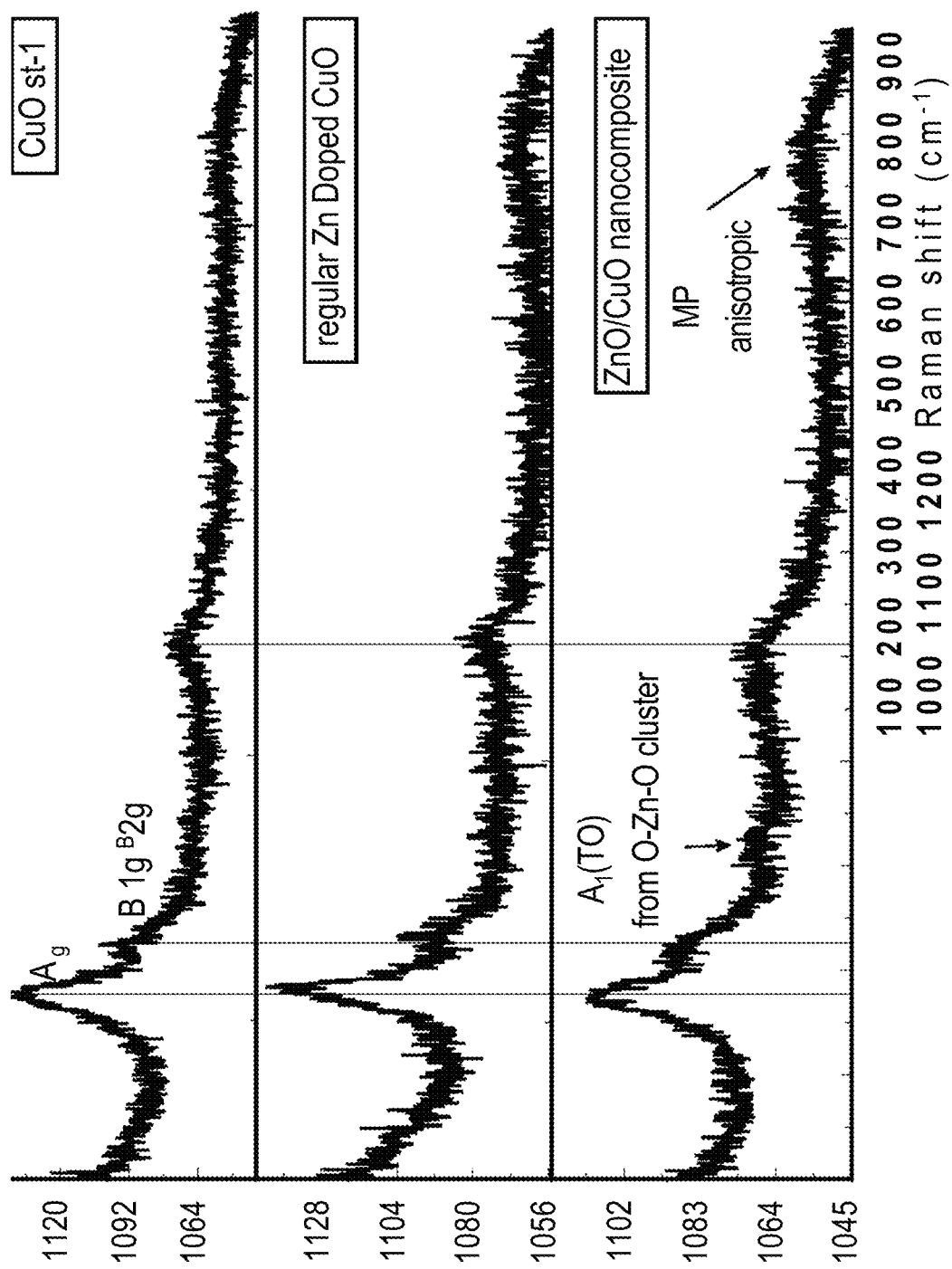
FIG. 3 is a comparison of Raman spectra for pure CuO, regular Zn doped CuO, and $CuO_{1-x}/ZnO_x$. From this comparison, the loss of symmetry on the whole structure (broad signals), new peaks related with the presence of O—Zn—O clusters, and probable presence of heterojunction due to the increment of multiphoton mode MP that is evidence of anisotropic conduction of electrons is shown.
Figure 4:
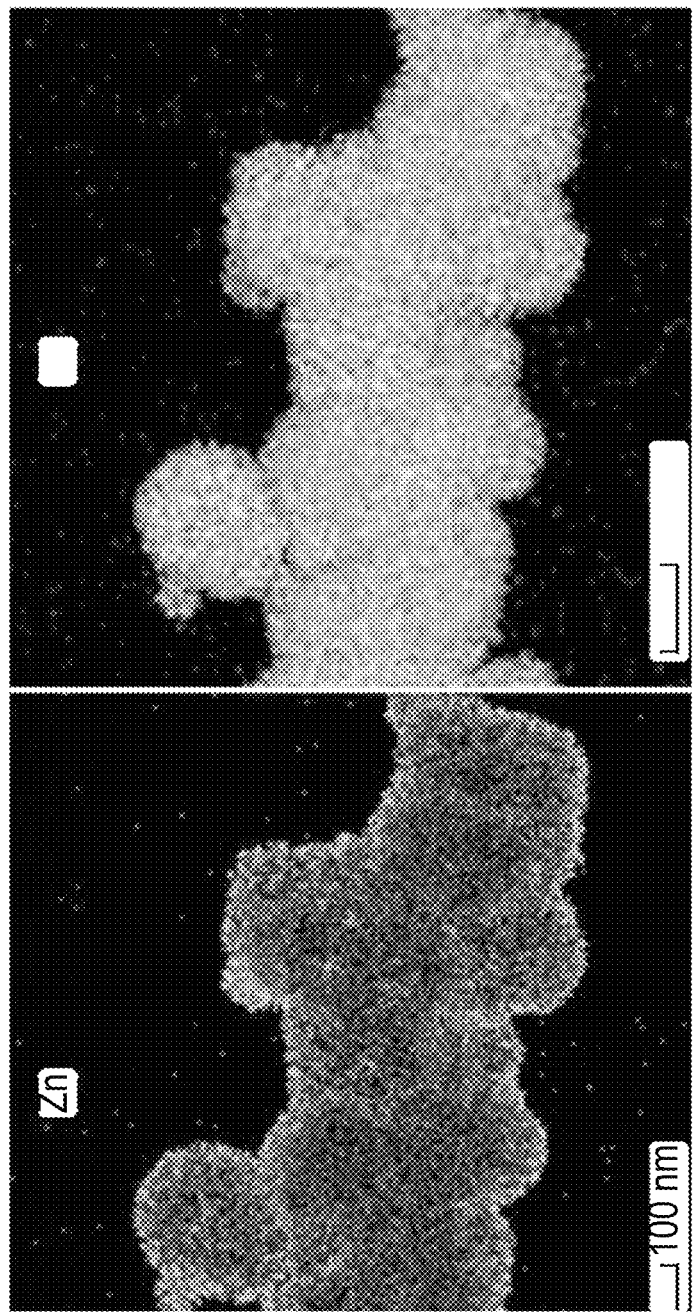
FIG. 4 is a High-resolution transmission electron microscopy (HR-TEM) with EDS detection for Zn and Cu which shows a non-homogenous distribution of those components and a clear core/shell structure.
Figure 5:
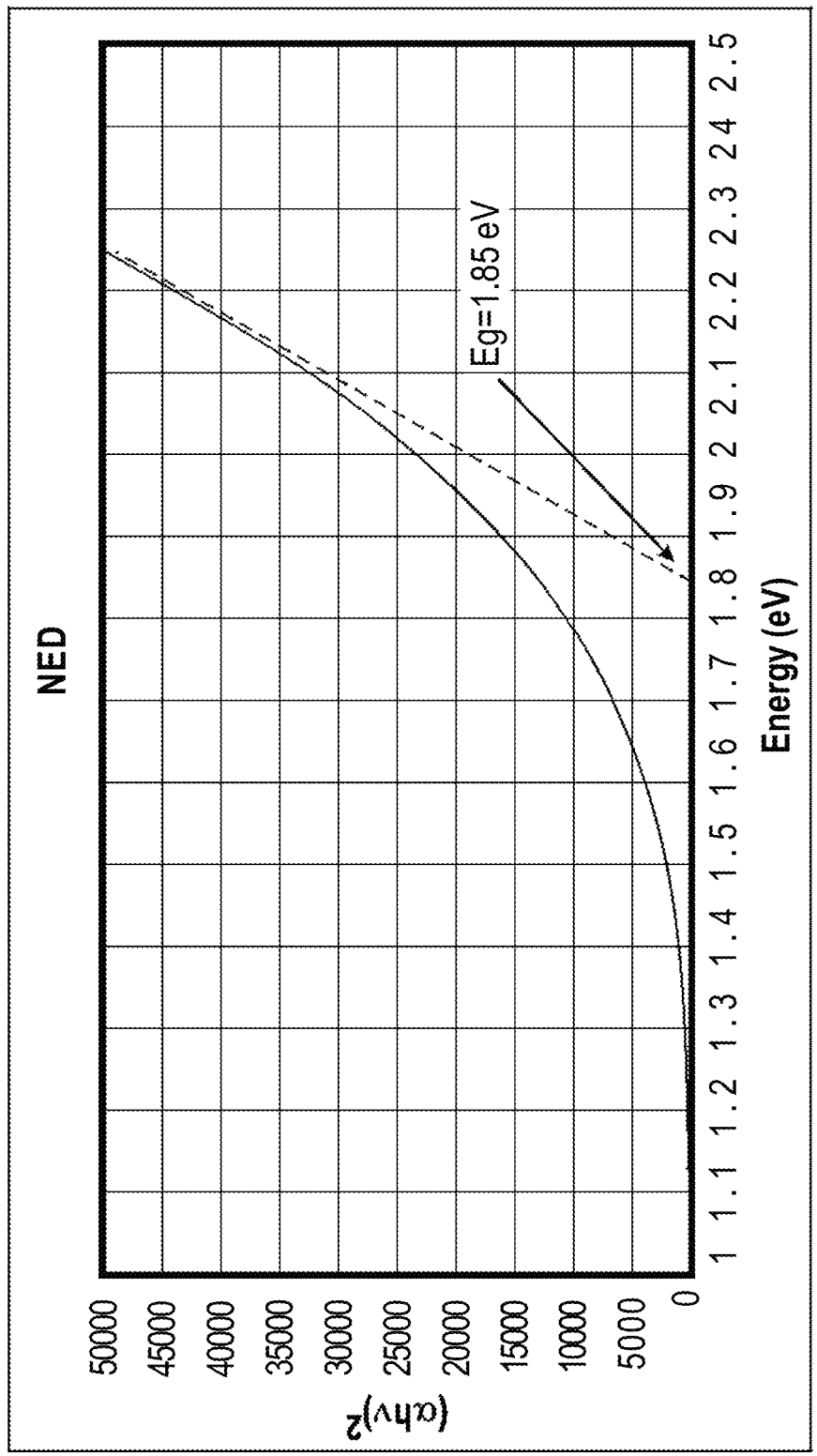
FIG. 5 shows the optical band gap $E_g$ calculation from the UV-vis spectrum of the metal oxide nanomaterials.
Figure 6:
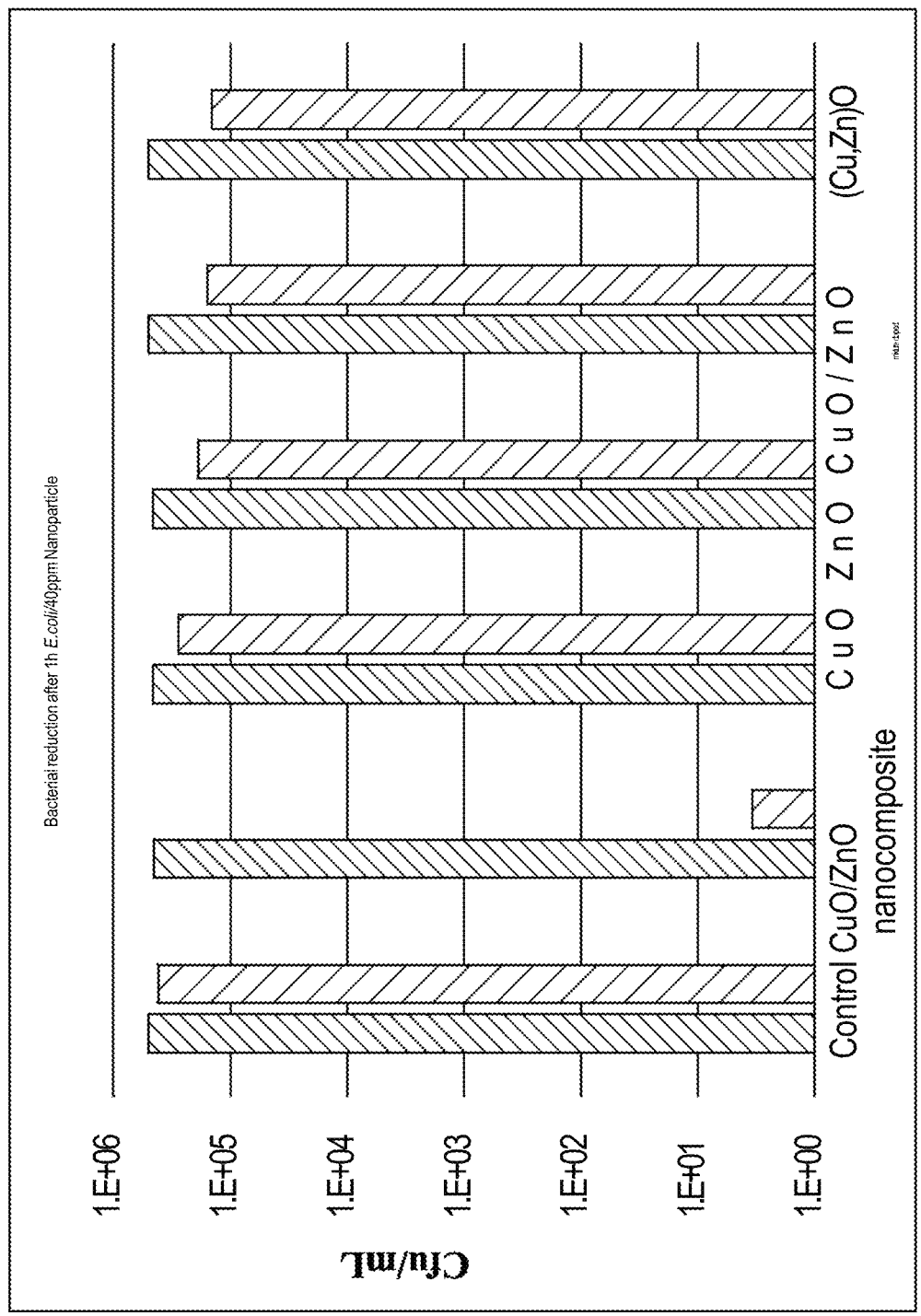
FIG. 6 is a representation showing the bactericidal activity against *E. coli* in saline and 5% fetal bovine serum (FBS) to simulate the wound fluid conditions according to ISO requirement. In both cases, within one hour of exposure, a total elimination of the *E. coli* in saline and 5% fetal bovine serum (FBS) was seen.
Figure 7:
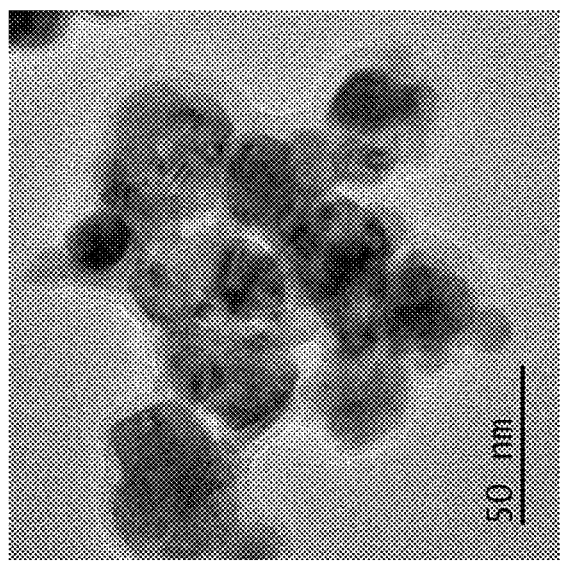
FIG. 7 shows a picture of a hemostatic polymer coated on the $CuO_{1-x}/ZnO_x$.

One aspect of the present disclosure encompasses a metal oxide semiconductor nanomaterial composition comprising a metal oxide nanomaterial and at least one hemostatic polymer wherein the metal oxide A and the metal oxide B are independently selected from a group comprising an alkaline earth metal, a d-block transition metal, f-block metal or combinations thereof; wherein the nanomaterial comprises clusters of metal oxide quantum dots, and wherein the hemostatic polymer is adhered or coated on the metal oxide semiconductor nanomaterial.

Another aspect of the present disclosure encompasses a metal oxide semiconductor nanomaterial composition comprising a metal oxide nanomaterial and at least one hemostatic polymer; wherein the metal portion of metal oxide A and the metal portion of metal oxide B are independently selected from a group consisting titanium, manganese, nickel, silver, calcium, magnesium, zinc, copper, or combinations thereof; wherein the nanomaterial comprises clusters of metal oxide quantum dots; and wherein the hemostatic polymer is adhered or coated on the metal oxide semiconductor nanomaterial.

Still another aspect of the present disclosure encompasses a metal oxide semiconductor nanomaterial composition comprising a CuO and ZnO nanomaterial and at least one hemostatic polymer wherein the nanomaterial comprises clusters of CuO and ZnO quantum dots comprising heterojunctions comprise at least one n-type metal oxide nanoparticle and at least one p-type metal oxide nanoparticle; and wherein the hemostatic polymer is adhered or coated on the metal oxide semiconductor nanomaterial.

Other features and iterations of the invention are described in more detail below.

DETAILED DESCRIPTION OF THE INVENTION

In one aspect, disclosed herein, are compositions of a metal oxide semiconductor nanomaterial composition comprising a metal oxide nanomaterial and at least one hemostatic polymer wherein the metal oxide semiconductor nanomaterial composition comprises metal oxide A and the metal oxide B are independently selected from a group comprising an alkaline earth metal, a d-block transition metal, f-block metal or combinations thereof; wherein the nanomaterial comprises clusters of metal oxide quantum dots, and wherein the hemostatic polymer is adhered or coated on the metal oxide semiconductor nanomaterial These combinations of metal oxides semiconductor nanomaterial and the hemostatic polymer provide many beneficial attributes such as a narrow optical band-gap, inhomogeneous electrical conductivity, a porous structure, relatively large surface area per unit of mass, a large surface area per unit of volume, and coagulation properties. The nanomaterials additionally release reactive oxygen species such that these nanomaterials exhibit antimicrobial properties, antibacterial properties, antifungal properties, or combinations thereof.

(I) Composition

The metal oxide semiconductor nanomaterial, described below, comprises at least two metal oxides, metal oxide A and metal oxide B. These nanomaterials comprise clusters of metal oxide quantum dots.

(a) Metal Oxide Semiconductor Nanomaterial

The metal oxide semiconductor nanomaterial comprises a metal oxide A and a metal oxide B wherein the nanomaterial are clusters of metal oxide quantum dots.

A wide variety of metal oxides may be used as metal oxide A and metal oxide B. In various embodiments, metal oxide A and metal oxide wherein the metal portion of metal oxide A and the metal portion of metal oxide B are independently selected from a group comprising an alkaline earth metal, a d-transition metal, f-transition, or combinations thereof. Non-limiting examples of suitable metal portion of alkaline earth metal oxides may be beryllium, magnesium, calcium, strontium, or barium. Non-limiting examples of the metal portion of suitable transition metal oxides may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide or zinc.

In preferred embodiments, metal oxide A and metal oxide B wherein the metal portion of metal oxide A and the metal portion of metal oxide B are independently selected from a group consisting of titanium, manganese, nickel, silver, calcium, magnesium, zinc, copper, or combinations thereof.

In particularly preferred embodiments, metal oxide A and metal oxide B wherein the metal portion of metal oxide A and the metal portion of metal oxide B are independently selected from a group consisting of zinc, copper, or combinations thereof. The copper-zinc mixed oxide nanomaterial has a chemical formula of $Cu_{1-x}O/ZnO_x$, wherein x is the atomic ratio of the zinc oxide impurities on the nanomaterial. Generally, the value of x may range from about 0.01 to about 0.26. In various, the value of X may range from about 0.01 to about 0.26, or from about 0.03 to about 0.24. In a preferred embodiment, the value of x may be around 0.2.

The crystalline structure of the copper oxide and/or the copper-zinc mixed oxide $Cu_{1-x}O/Zn_xO$ is modified tenorite. In the modified tenorite structure, zinc oxide clusters may intercalate some of copper oxide crystal lattice as interstitial impurities. Tenorite is the crystal structure of copper oxide CuO.

The crystal structure of the metal oxide can be determined by method known in the art. Non-limiting methods for determination of the crystal structure may be Raman spectrometry, high resolution transition electron microscopy (HR-TEM/EDS), x-ray crystallography, or combinations thereof.

As appreciated by the skilled artisan, the nanomaterial comprises two regions, where one region is the surface region and the second region is the core region of the nanomaterial. Preferably, the surface region of the nanomaterial completely encloses the core region of the nanomaterial. The distribution of these metal oxides can and will vary. In one embodiment, metal oxide A is substantially distributed in the core region of the nanomaterial while metal oxide B is substantially distributed in the surface region. In another embodiment, metal oxide A is substantially distributed in the surface region of the nanomaterial while metal oxide B is substantially distributed in the core region.

In various embodiments, metal oxide A is substantially distributed in the core region of the nanomaterial while metal oxide B is substantially distributed in the surface region. Generally, the surface region comprises more than 10% by weight of metal oxide B and less than 90% by weight of metal oxide A. In various embodiments, the surface region comprises more than 10% by weight, more than 20% by weight, or more than 25 weight % of metal oxide B. The core region comprises less than 90% by weight of metal oxide A. In various embodiments, the core region comprises less than 90% by weight, less than 80% by weight, or less than 75% by weight of metal oxide A. In a preferred embodiment, the surface region comprises about 27%±3% by weight of metal oxide B and the core region comprises 73%±3% by weight of metal oxide A.

In other embodiments, metal oxide A is substantially distributed in the surface region of the nanomaterial while metal oxide B is substantially distributed in the core region. In general, the surface region comprises more than 80% by weight of metal oxide A. In various embodiments, the surface region comprises more than 80% by weight, more than 85% by weight, or more than 90% by weight of metal oxide A. The core region comprises less than 20% by weight of metal oxide B. In various embodiments, the core region comprises less than 20% by weight, less than 15% by weight, or less than 10% by weight. In a preferred embodiment, the surface region comprises about 93%±1% of metal oxide A and the core region comprises about 9%+1% of metal oxide B.

The distribution of the metal oxide B and metal oxide A in the metal oxide semiconductor nanomaterial may be determined by characterization methods known in the art. Non-limiting examples of suitable characterization methods may be scanning electron microscopy (SEM), energy-dispersion X-ray spectroscopy (EDS), transmission electron microscopy (TEM), or combination thereof.

As appreciated by the skilled artisan, a mixture of the nanomaterials may be present in the composition. Overall, the mass content of metal oxide B in the nanomaterial may range from about 10% by weight to about 30% by weight. In various embodiments, the mass content of metal oxide B in the nanomaterial may range from about 10% to about 30% by weight or from about 15% by weight to about 25% by weight. In a preferred embodiment, the mass content of metal oxide B in the nanomaterial may be about 18%±4% by weight.

The metal oxide nanomaterial is a semiconductor. The semiconductor comprises at least one n-type metal oxide nanoparticle and at least one p-type nanoparticle. As appreciated by the skilled artisan, an n-type metal oxide is a semiconductor metal oxide in which most charge carriers are electrons, whereas a p-type metal oxide is a semiconductor metal oxide in which most charge carriers are electron holes. Preferably, the metal oxide semiconductor nanomaterial comprises heterojunctions unions between the n-type and the p-type semiconductors. As appreciated by the skilled artisan, heterojunctions are interfaces between two dissimilar crystalline semiconductors which have unequal band gaps.

The metal oxide semiconductor nanomaterial shows an inhomogeneous electrical conductivity. The inhomogeneous electrical conductivity may be the result of an inhomogeneous distribution of the metal oxide B in the surface region of the metal oxide semiconductor nanomaterial or may be result from an inhomogeneous distribution of the metal oxide A in the surface region of the metal oxide semiconductor nanomaterial.

Quantum dots exhibit properties that are an intermediate between those of bulk semiconductors and those of discrete atoms or molecules. Quantum dots are very small semiconductor particles having nanometer size. Quantum dots are also semiconductor nanocrystals. The semiconductor nanomaterials of the present invention comprise semiconductor particles of nanometer size, nanocrystals, or combinations thereof. In other words, any semiconductor metal oxide may be synthesized as quantum dots.

(b) Hemostatic Polymer Material, Organic Molecule, or Combinations Thereof

The metal oxide semiconductor nanomaterial may further comprise at least one polymer material, at least one organic molecule, or combinations thereof. In some embodiments, the nanomaterial may be dispersed in the at least one polymer, at least one organic molecule, or combinations thereof. In other embodiments, the metal oxide at the surface of the nanomaterial may be functionalized with the at least one polymer, at least one organic molecule, or combinations thereof. In either case, the metal oxide semiconductor nanomaterial may be used in many different applications and environments.

A wide variety of polymer materials and organic molecules may be used with the metal oxide nanomaterial. Non-limiting examples of suitable polymer materials may be chitosan, alginate, gelatin, carboxymethyl cellulose, polyethylene glycol, or combinations thereof. Non-limiting examples of suitable organic molecules may be octadecanethiol, perfluorothiol, cysteine, mercaptoalkanes, citric acid, oleic acid, or combinations thereof. In one preferred embodiment, the at least one polymer is a hemostatic polymer. Non-limiting examples of hemostatic polymers may be chitosan, alginate, gelatin, carboxymethyl cellulose, polyethylene glycol, collagen, alginic acid, poly(cyanacrylate)s, (polyalkylene oxide)s, or salts thereof.

Generally, the weight % (wt %) of the at least one polymer material, at least one organic molecule, or combinations thereof dispersed or functionalized on the metal oxide semiconductor nanomaterial may range from about 1 wt % to about 5 wt %. In various embodiments, the weight % (wt %) of the at least one polymer material, at least one organic molecule, or combinations thereof dispersed or functionalized on the metal oxide semiconductor nanomaterial may range from about 1 wt % to about 5 wt %, from about 2 wt % to about 4 wt %, or from about 2.5 wt % to about 3.5 wt %. In one preferred embodiment, the weight % (wt %) of the at least one polymer material, at least one organic molecule, or combinations thereof dispersed or functionalized on the metal oxide semiconductor nanomaterial may be about 3 wt %.

In general, the thickness of the at least one polymer, at least one organic molecule, or combinations thereof may range from about 1.0 nm to about 10.0 nm. In various embodiments, the thickness of the at least one polymer, at least one organic molecule, or combinations thereof may range from about 1.0 nm to about 10.0 nm, from about 2.0 nm to about 8.0 nm, or from about 3.0 to about 6.0 nm.

(c) Properties of the Metal Oxide Semiconductor Nanomaterial

The nanomaterial, as described above, exhibits many useful and unique properties.

Generally, the optical band gap of the metal oxide semiconductor nanomaterial may range from about 0.5 eV to 6.5 eV. In various embodiments, the optical band gap of the metal oxide semiconductor nanomaterial may range from about 0.5 eV to 6.5 eV, from about 1.0 eV to 4.0 eV, from about 1.2 eV to 2.1 eV, or from about 1.74 eV to 1.85 eV. In a preferred embodiment, the optical band gap of the metal oxide semiconductor nanomaterial may be about 1.8 eV.

The metal oxide semiconductor nanomaterial comprises a mesoporous structure at a nanometer scale, a large surface area per unit of mass ($m^2/g$), a large surface area per unit of volume ($m^2/mL$), or combinations thereof. Generally, the surface area of the metal oxide semiconductor nanomaterial may be larger than 20 $m^2/g$. In various embodiments, the surface area of the metal oxide semiconductor nanomaterial may be larger than about 20 $m^2/g$, or larger than about 40 $m^2/g$. In a preferred embodiment, the surface area of the metal oxide semiconductor nanomaterial may range from about 40 $m^2/g$.

Generally, the size of or at least one dimension of metal oxide semiconductor nanoparticle may range from about 1 nanometers to 10,000 nanometers. In various embodiments, the size of or at least one dimension of metal oxide semiconductor nanoparticle may range from about 1 nanometer to 10,000 nanometers, from about 10 nanometers to about 5,000 nanometers, or from about 100 nanometers to about 1,000 nanometers. In one embodiment, the size of or at least one dimension of metal oxide semiconductor nanoparticle may range from about 10 nanometers to 1,000 nanometers. In a preferred embodiment, the size of or at least one dimension of metal oxide semiconductor nanoparticle may range from about 10 nanometers to about 150 nanometers.

In general, the thickness of the surface region may range from about 1 nm to about 1000 nm. In various embodiments, the thickness of the surface area may range from about 1 nm to about 1000 nm, from about 10 nm to about 50 nm, or from about 15 nm to about 45 nm. In a preferred embodiment, the thickness of the surface area may be about 30 nm.

The metal oxide semiconductor nanomaterial exhibits antimicrobial properties, antibacterial properties, antifungal properties, or a combination thereof. Upon contact of the metal oxide semiconductor nanomaterial with a microorganism, a bacterium, fungus, and a combination thereof, the metal oxide semiconductor nanomaterial releases a reactive oxygen species. Non-limiting examples of the reactive oxygen species may be oxygen, a superoxide anion, a peroxide anion, a hydroxyl radical, and any combination thereof. These reactive oxygen species, once in contact with a microorganism, a bacterium, or a fungus, can cause damage to cells through oxidative damage. These metal oxide semiconductor nanomaterials present a positively charge surface, which might interact with the negatively charged bacterial membrane and cause physical damage and membrane permeability disruption by electrostatic interactions with the microorganism.

The antimicrobial properties, antibacterial properties, antifungal properties, or a combination thereof of the metal oxide semiconductor nanomaterials is defined as a bactericidal effect expressed as percentage of mortality against a specific kind of bacteria for a specific duration of time in a specific concentration. Generally, the average of mortality rate of the nanomaterial against *Escherichia coli* over from 1 to 24 hour time period may be larger than about 50%. In various embodiments, the average mortality rate of the nanomaterial against *Escherichia coli* over an hour time period may be larger than about 90%, larger than about 95%, larger than 99%, larger than about 99.9%, or larger than 99.99%. In a preferred embodiment, the average mortality rate of the nanomaterial against *Escherichia coli* over an hour time period may be larger than about 99.99%.

The coated or adhered metal oxide semiconductor nanomaterial with at least one polymer, at least one organic molecule, or combinations thereof exhibit unique properties. In one preferred embodiment, the at least one polymer, at least one organic molecule, or combinations thereof may be a hemostatic polymer. Specific hemostatic polymers are described above. The hemostatic polymer provides additional attributes such as blood coagulation.

The surface ζ-potential for 100 ppm water suspension of chitosan functionalized or coated on the metal oxide semiconductor nanomaterial may range from +10 mV to about +30 mV. In various embodiments, the surface ζ-potential for 100 ppm water suspension of chitosan functionalized or coated on the metal oxide semiconductor nanomaterial may range from +10 mV to about +30 mV, from about +15 mV to about +25 mV, or about +20 mV.

The surface ζ-potential for 100 ppm water suspension of calcium alginate functionalized or coated on the metal oxide semiconductor nanomaterial may range from −40 mV to about 0 mV. In various embodiments, the surface ζ-potential for 100 ppm water suspension of calcium alginate functionalized or coated on the metal oxide semiconductor nanomaterial may range from −40 mV to about 0 mV, from about −30 mV to about −10 mV, or about −20 mV.

The antimicrobial activity for the hemostatic polymer coated or adhered on the metal oxide semiconductor nanomaterial in a 40 ppm suspension of *Escherichia coli* may be at least 95%. In various embodiments, the antimicrobial activity for the hemostatic polymer dispersed or functionalized on the metal oxide semiconductor nanomaterial in a 40 ppm suspension of *Escherichia coli* may be at least 95%, at least 97.5%, at least 99%, or at least 99.999%. In one preferred embodiment, the antimicrobial activity for the hemostatic polymer coated or adhered on the metal oxide semiconductor nanomaterial in a 40 ppm suspension of *Escherichia coli* is at least 99.999% or not less than a 5 log reduction.

(II) Processes for Preparing the Metal Oxide Semiconductor Nanomaterial

In another aspect, disclosed herein, are processes to prepare the metal oxide semiconductor nanomaterial. The process comprises: (a) providing a first aqueous solution comprising a soluble metal salt A and a soluble metal salt B; (b) providing a second aqueous solution comprising at least one soluble anion; (c) admixing the second aqueous solution with the first aqueous solution to form an insoluble precursor metal oxide semiconductor nanomaterial; (d) isolating the metal oxide semiconductor nanomaterial precursor; (e) drying the metal oxide semiconductor precursor; (f) thermal decomposition of the metal oxide semiconductor precursor to form the metal oxide semiconductor nanomaterial; (g) coating or adhering the hemostatic polymer on the surface of the metal oxide semiconductor nanomaterial; and (h) drying the hemostatic polymer coated or adhered on the metal oxide semiconductor nanomaterial. The process may be conducted in batch, semi-continuous, or continuous mode.

(a) First Aqueous Solution

The process commences by preparing the first aqueous solution comprising a soluble metal salt A and a soluble metal salt B.

As appreciated by the skilled artisan, the soluble metal salts A and B are transformed into metal oxide A and metal oxide B after completion of the process.

A wide variety of soluble metal salts may be used in the process to prepare metal oxide A and metal oxide B. In various embodiments, soluble metal salt A and soluble metal salt B wherein the metal portion of these salts are independently selected from a group comprising an alkaline earth metal, a transition metal, or combinations thereof. Non-limiting examples of suitable metal portion of alkaline earth metal salts may be beryllium, magnesium, calcium, strontium, or barium. Non-limiting examples of the metal portion of suitable transition metal salts may be scandium, titanium vanadium, chromium, manganese, iron, cobalt, nickel, copper, yttrium, zirconium, platinum, gold, mercury, niobium, iridium, molybdenum, technetium, ruthenium, rhodium, palladium, silver, cadmium, hafnium, tantalum, tungsten, rhenium, osmium, any lanthanide, or zinc.

In preferred embodiments, soluble metal salt A and soluble metal salt B wherein the metal portion of these salts are independently selected from a group consisting of titanium, manganese, nickel, silver, calcium, magnesium, zinc, copper, or combinations thereof.

In particularly preferred embodiments, soluble metal salt A and soluble metal salt B wherein the metal portion of these salts are independently selected from a group consisting of zinc, copper, or combinations thereof.

A wide variety of anions may be used for soluble metal salt A and soluble metal salt B. An important aspect of these anions is that the anion is readily exchangeable, soluble in aqueous solution, non-toxic, pH neutral, and thermally decomposable. Non-limiting examples of suitable anions may be acetate, propionate, any soluble organic salt or combinations thereof. In a preferred embodiment, the anions used for soluble metal salt A and soluble metal salt B is acetate.

In other embodiments, the first aqueous solution may further comprise one or more different soluble salts than the soluble salts A and soluble salts B as described above.

The molar ratio of the soluble metal salt A to the soluble metal salt B may range from about 12:1 to about 1:12. In various embodiments, the molar ratio of the soluble metal salt A to the soluble metal salt B may range from about 12:1 to about 1:12, from about 11:1 to about 1:11, from about 10:1 to about 1:10, from about 9:1 to about 1:9, from about 8:1 to about 1:8, from about 7:1 to about 1:7, from about 7:1 to about 1:7, from about 6:1 to about 1:6, from about 5:1 to about 1:5, from about 4:1 to about 1:4, from about 3:1 to about 1:3, or from about 2:1 to about 1:2. In a preferred embodiment wherein soluble metal salt A is copper and the soluble metal salt B is zinc, the molar ratio may be about 2.3:1.

In general, the concentration of soluble metal salt A, soluble metal salt B, or combinations thereof in water may range from about 0.01M (moles/liter) to about 1.0M. In various embodiments, the concentration of the soluble metal salt A and soluble metal salt B may range from about 0.01M to about 1.0M, 0.03M to about 0.3M, or from 0.05M to 0.15M. In a preferred embodiment, the concentration of soluble metal salt A, soluble metal salt B, or combinations thereof in water may be about 0.15M.

The first aqueous solution may further comprise a stabilizer. Non-limiting examples of stabilizers may be a polyethylene glycol (PEG), polypropylene glycol (PPG), polyvinylpyrrolidone (PVP), polyvinylalcohol (PVA), Polyoxyethylene or combinations thereof. In a preferred embodiment, the stabilizer used in the first aqueous solution further comprises PEG, specifically PEG4000.

The concentration of the stabilizer in the first aqueous solution may range from about 0.0001M to about 0.001M. In various embodiments, the concentration of the stabilizer in the first aqueous solution may range from about 0.0001M to about 0.001M. In a preferred embodiment, the concentration of the stabilizer in the first aqueous solution may be preferably about 0.0007M.

The preparation of the first solution may be achieved by blending the soluble metal salt A, soluble metal salt B, water, an optional stabilizer, and an optional solvent in any known mixing equipment or reaction vessel until the mixture achieves homogeneity. These components may be added all at the same time, sequentially, or in any order.

In general, the preparation of the first aqueous solution may be conducted at a temperature that ranges from about 10° C. to about 40° C. In various embodiments, the temperature of the reaction may range from about 10° C. to about 40° C., from about 15° C. to about 35° C., or from about 20° C. to about 30° C. In one embodiment, the temperature of the reaction may be about room temperature (~23° C.). The reaction typically is performed under ambient pressure. The reaction may also be conducted under an inert atmosphere or air, for example under nitrogen, argon or helium.

The duration for preparing the first aqueous solution and will vary depending on many factors, such as the temperature, the method of mixing, and amount of materials being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours. In various embodiments, the preparation may be allowed to continue until the first aqueous solution obtains homogeneity.

(b) Second Aqueous Solution

The second aqueous solution comprises at least one soluble anion source. An important aspect of these soluble anions is that anion is readily exchangeable, soluble in aqueous solution, is non-toxic, pH neutral, and thermally decomposable. Non-limiting examples of suitable anion sources may be lithium bicarbonate, sodium bicarbonate, potassium bicarbonate, and ammonium bicarbonate, or any alkaline oxalate, alkaline malate. In a preferred embodiment, the second aqueous solution comprises ammonium bicarbonate.

The second aqueous solution may be prepared by forming a reaction mixture comprising at least one soluble anion source, water, and optionally ethanol. These components may be added all at the same time, sequentially, or in any order. The second aqueous solution may be achieved by blending the above components in any known mixing equipment or reaction vessel until the mixture achieves a clear solution.

In general, the preparation of the second aqueous solution may be conducted at a temperature that ranges from about 10° C. to about 40° C. In various embodiments, the temperature of the preparation may range from about 10° C. to about 40° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The duration for preparing the second aqueous solution and will vary depending on many factors, such as the temperature, the method of mixing, and amount of the at least one anion source being mixed. The duration of the reaction may range from about 5 minutes to about 12 hours. In some embodiments, the duration of the reaction may range from about 5 minutes to about 30 minutes, from about 30 minutes to about 2 hours, from about 2 hours to about 4 hours, from about 4 hours to about 10 hours, or from about 10 hours to about 12 hours.

Generally, the concentration of the at least one soluble anion source in the second aqueous solution may range from a concentration of about 0.10M to about 1.5M. In various embodiments, the concentration of the at least one soluble anion source in the second aqueous solution may range in a concentration from about 0.10M to about 1.5M, from about 0.2M to about 1.4M, or from about 0.3M to about 1.2M. In a preferred embodiment, the concentration of the at least one soluble anion source in the second aqueous solution may be about 0.3M.

(c). Preparation of the Insoluble Metal Oxide Semiconductor Nanomaterial Precursor.

The next step in the process is to prepare the insoluble metal oxide semiconductor nanomaterial precursor. Preparing the insoluble metal oxide semiconductor nanomaterial precursor occurs when the second aqueous solution comprising the at least one anion source is admixed with the first aqueous solution. As appreciated by the skilled artisan, once the second aqueous solution is admixed with the first aqueous solution, a chemical reaction occurs. In a preferred embodiment, the metal oxide semiconductor nanomaterial precursor comprising a copper zinc mixed carbonates are formed and can be depicted according to the following scheme.

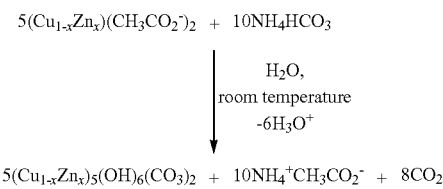

As appreciated by the skilled artisan, an advantage of using ammonium salt in the second aqueous solution is that by product, ammonium acetate, is water soluble, easily removed from the metal oxide semiconductor nanomaterial precursor, neutral pH at room temperature, and trace amount of ammonium acetate are readily thermally decomposed in the process.

The process may further comprise an organic solvent. The purpose of the solvent in the process is to reduce the foaming as the two aqueous solutions are combined, namely carbon dioxide. The addition of solvent may also cause a sudden change of the dielectric constant and change the dynamic of precipitation of the insoluble metal oxide semiconductor nanomaterial precursor. These changes may further lead to a hierarchic structure, a core-shell configuration of the metal oxide semiconductor nanomaterial, or combinations of both of properties. An additional property of the solvent is that solvent is volatile so excess amounts of solvent may be readily removed. Non-limiting examples of suitable solvents may be methanol, ethanol, propanol, iso-propanol, acetone or combinations thereof. In a preferred embodiment, the solvent in the process is ethanol.

Generally, the volume percent of the solvent in the mixture of the first aqueous solution, the second aqueous solution or combinations thereof may range from about 0.01 volume % to about 0.1 volume % In various embodiments, the volume percent of the solvent in the mixture of the first aqueous solution, the second aqueous solution or combinations thereof may range from about 0.01 volume % to about 0.1 volume %, from about 0.02 volume % to about 0.08 volume %, or from about 0.03 volume % to about 0.07 volume %. In a preferred embodiment, the volume percent of the solvent in the mixture of the first aqueous solution, the second aqueous solution or combinations thereof may be about 0.02 volume %.

The solvent may be added to the first aqueous solution, the second aqueous solution, or the combination of the first aqueous solvent and the second aqueous solvent, or combinations thereof.

The metal oxide semiconductor nanomaterial precursor may be prepared by forming a reaction mixture comprising the first aqueous solution, the second aqueous solution, and the optional solvent. The metal oxide semiconductor nanomaterial precursor may be achieved by blending the above components in any known mixing equipment or reaction vessel or static mixer until the mixture achieves completeness of reaction.

In an embodiment, the second aqueous solution may be added to the first solution. Generally, the second aqueous solution is added immediately in a batch o by a static mixer continuously in a range from about 20 volume % to about 45 volume % to the first aqueous solution. In a speed from 1 to 10 l/min, in various embodiments form 1.25 to 8 l/min. In a preferred embodiment 5 to 6 l/min. This quick addition ensures the chemical reaction depicted above goes to completion.

Since the insoluble metal oxide semiconductor nanomaterial precursor precipitates from an aqueous solution, the method of stirring to prepare the precursor is important so amounts of the soluble metal salt A, metal salt B, or the at least one soluble anion source does not become entrained in the insoluble metal oxide semiconductor nanomaterial precursor. Generally, the process may be stirred mechanically at a speed from about 250 rpm (revolution per minute) to about 1000 rpm. In various embodiments, the stirring speed may range from 250 rpm to about 1200 rpm, from about 300 rpm to about 1000 rpm, or from about 500 rpm to about 900 rpm. Ina preferred embodiment, the stirring speed of the process may be about 700 rpm.

In general, the preparation of the insoluble metal oxide semiconductor nanomaterial precursor may be conducted at a temperature that ranges from about 10° C. to about 65° C. In various embodiments, the temperature of the preparation may range from about 10° C. to about 65° C., from about 15° C. to about 35° C., or from about 20° C. to about 30° C. In one embodiment, the temperature of the preparation may be about room temperature (~23° C.). The preparation typically is performed under ambient pressure. The preparation may also be conducted under air or an inert atmosphere, for example under nitrogen, argon or helium.

The pH during the addition of the reaction between the second aqueous solution and the first aqueous solution may range from about 6.0 to about 8.0. In various embodiments, the pH of the process may range from about 6.0 to about 8.0, from about 6.5 to about 7.5, or from about 6.7 to about 7.3. In a preferred embodiment, the pH of the process is about 6.8 to 7.0.

The duration for preparing the insoluble metal oxide semiconductor nanomaterial precursor and will vary depending on many factors, such as the temperature, the method of mixing, and scale of the process. The duration of the reaction may range from about 5 minutes to about 6 hours. In some embodiments, the duration of the reaction may range from about 5 minutes to about 6 hours, from about 15 minutes to about 4 hours, or from about 20 minutes to about 1 hour. In a preferred embodiment, the duration for preparing the insoluble metal oxide semiconductor precursor may be about 30 minutes.

(d) Isolating the Insoluble Metal Oxide Semiconductor Nanomaterial Precursor

The next step in the process is isolating the insoluble metal oxide semiconductor nanomaterial precursor from the reaction mixture in step (c) comprising water, the stabilizer, and the optional solvent. As appreciated by the skilled artisan, there are many methods of isolating the insoluble metal oxide semiconductor nanomaterial precursor from the reaction mixture in step (c). Non-limiting methods may be filtration, centrifugal separation, decantation, or combinations thereof. The insoluble metal oxide semiconductor nanomaterial precursor, after isolation, may be rinsed with water, ethanol, or combinations thereof. The precursor is washed with water, ethanol, or combinations thereof solvent until the supernatant is colorless or the precursor color remains constant.

(e) Drying the Insoluble Metal Oxide Semiconductor Precursor.

The next step in the process is drying the insoluble metal oxide semiconductor nanomaterial precursor from the reaction mixture in step (d). This step would remove excess amounts of solvent from the insoluble metal oxide semiconductor nanomaterial precursor. As appreciated by the skilled artisan, many devices are available to dry the precursor. Non-limiting examples for drying the solid may be batch driers, convection ovens, rotary dryers, drum dryers, kiln dryers, flash dryers, or tunnel dryers.

In general, the drying of the insoluble metal oxide semiconductor nanomaterial precursor may be conducted at a temperature that ranges from about 30° C. to about 120° C. In various embodiments, the temperature of the preparation may range from about 30° C. to about 120° C., from about 40° C. to about 100° C., or from about 50° C. to about 80° C. In one embodiment, the temperature of drying may be about 60° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 30 minutes to about 48 hours. In some embodiments, the duration of the reaction may range from about 30 minutes to about 48 hours, from about 1 hour to about 24 hours, or from about 2 hours to about 4 hours. In a preferred embodiment, the duration for drying the insoluble metal oxide semiconductor precursor may be about 3 hours, or until the drying the insoluble metal oxide semiconductor precursor reaches less than 12% moisture.

(f) Thermal Decomposition of the Insoluble Metal Oxide Semiconductor Nanomaterial Precursor Forming the Metal Oxide Semiconductor Nanomaterial The next step in the process is thermal decomposition of the insoluble metal oxide semiconductor nanomaterial precursor forming the metal oxide semiconductor nanomaterial. This step removes transforms the thermally labile ligand forming the oxides and removes by-products and impurities that were not removed in step (d). As appreciated by the skilled artisan, carbon, hydrogen and excessive oxygen may be released in forms of carbon dioxide and water steam from the thermally labile ligands, by-products, and impurities. In a preferred embodiment, the metal oxide semiconductor nanomaterial precursor comprising a copper zinc mixed oxide is thermally decomposed to form the metal oxide semiconductor nanomaterial. This reaction can be depicted according to the following scheme.

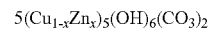

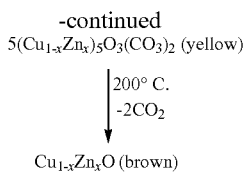

$5(Cu_{1-x}Zn_x)_5O_3(CO_3)_2$ (yellow)

$\downarrow$ 200° C. / $-2CO_2$ $Cu_{1-x}Zn_xO$ (brown)

In general, thermal decomposition of the insoluble metal oxide semiconductor nanomaterial precursor may be conducted at a temperature that ranges from about 200° C. to about 1000° C. In various embodiments, the temperature of the preparation may range from about 200° C. to about 1000° C., from about 225° C. to about 800° C., or from about 250° C. to about 350° C. In one embodiment, the temperature of drying may be about 300° C. The preparation typically is performed under ambient pressure. The preparation may also be conducted under air or an inert atmosphere, for example under nitrogen, argon or helium.

The duration for drying the insoluble metal oxide semiconductor nanomaterial precursor and will vary depending on many factors, such as the temperature, the amount of the precursor, and type of the dryer. The duration of the reaction may range from about 5 minutes to about 48 hours. In some embodiments, the duration of the reaction may range from about 10 minutes to about 48 hours, from about 15 hour to about 24 hours, or from about 2 hours to about 4 hours. In a preferred embodiment, the duration for drying the insoluble metal oxide semiconductor precursor may be about 0.3 hour.

The yield of the metal oxide semiconductor material from the process described above may range from 5 to 12 g/L. with high purity.

(g) Coating or Functionalizing the Hemostatic Polymer on the Surface of the Metal Oxide Semiconductor Nanomaterial The process may further comprise coating or adhering a hemostatic polymer on the metal oxide semiconductor surface. Various hemostatic polymers are described above. Method for coating or adhering the hemostatic polymer on the metal oxide semiconductor nanomaterial are known in the arts. In one embodiment, the hemostatic polymer may be dispersed with the metal oxide semiconductor nanomaterial, thereby coating or adhering the hemostatic polymer to the surface of the metal oxide semiconductor nanomaterial.

Generally, the weight % (wt %) of the hemostatic polymer on the metal oxide semiconductor nanomaterial surface may range from about 1 wt % to about 5 wt %. In various embodiments, the weight % (wt %) of the hemostatic polymer dispersed on the metal oxide semiconductor nanomaterial surface may range from about 1 wt % to about 5 wt %, from about 2 wt % to about 4 wt %, or from about 2.5 wt % to about 3.5 wt %. In one preferred embodiment, the weight % (wt %) of the hemostatic polymer on the metal oxide semiconductor nanomaterial surface may be about 3 wt %.

(h) Drying the Hemostatic Polymer Coated on the Metal Oxide Semiconductor Nanomaterial The process further comprises drying the hemostatic polymer coated or adhered on the surface of the metal oxide semiconductor nanomaterial. This step would remove excess amounts of solvent/water from the hemostatic polymer coated metal oxide semiconductor nanomaterial. As appreciated by the skilled artisan, many devices are available to dry the precursor. Non-limiting examples for drying the solid may be batch driers, convection ovens, rotary dryers, drum dryers, kiln dryers, flash dryers, or tunnel dryers.

In general, the drying of the hemostatic polymer coated or adhered on the metal oxide semiconductor nanomaterial may be conducted at a temperature that ranges from about 30° C. to about 120° C. In various embodiments, the temperature of the preparation may range from about 30° C. to about 120° C., from about 40° C. to about 100° C., or from about 50° C. to about 80° C. In one embodiment, the temperature of drying may be about 60° C. The preparation typically is performed under ambient pressure. The preparation may also be conducted under air or an inert atmosphere, for example under nitrogen, argon or helium.

The duration for drying the hemostatic polymer coated or adhered to the metal oxide semiconductor nanomaterial surface can and will vary depending on many factors, such as the temperature, the amount of the hemostatic polymer, and the type of the dryer. The duration of the reaction may range from about 30 minutes to about 48 hours. In some embodiments, the duration of the drying may range from about 30 minutes to about 48 hours, from about 1 hour to about 24 hours, or from about 2 hours to about 4 hours. In a preferred embodiment, the duration for drying of the hemostatic polymer coated metal oxide semiconductor nanomaterial may be about 3 hours to 6 hours.

(III) Methods for Using the Metal Oxide Semiconductor Nanomaterial

In still another aspect, disclosed herein, encompass methods of using the metal oxide semiconductor nanomaterial or the metal oxide semiconductor nanomaterial surface coated or adhered with the hemostatic polymer. The methods comprise coating an article such as fabrics bandages, coating textiles, catheters, and syringe needles with the metal oxide semiconductor nanomaterial or the metal oxide semiconductor nanomaterial surface coated on or adhered to the hemostatic polymer, hydrophobic coatings comprising the metal oxide semiconductor nanomaterial, creams for human and animal use, and photovoltaic cells comprising the metal oxide semiconductor nanomaterial. These metal oxide semiconductor nanomaterials may be further incorporated into paints or coatings.

In one embodiment, the method comprises coating an article such as fabric bandages, textiles, catheters, and needles with an effective amount of the metal oxide semiconductor nanomaterial or the metal oxide semiconductor nanomaterial surface coated or adhered with the hemostatic polymer. The method comprises dispersing the metal oxide semiconductor nanomaterial or the metal oxide semiconductor nanomaterial surface coated or adhered with the hemostatic polymer in the appropriate solvent (such as ethanol, water, or combinations thereof), spraying the dispersed metal oxide nanomaterial or the metal oxide semiconductor nanomaterial surface coated or adhered with the hemostatic polymer onto the article thereby forming a coating of the metal oxide semiconductor nanomaterial or the metal oxide semiconductor nanomaterial surface coated or adhered with the hemostatic polymer on the coating, and drying the coating to remove the solvent using heat, vacuum, an inert gas. Once the coating is applied to the article, the article provides antimicrobial properties, antibacterial properties, antifungal properties, or combinations thereof to the article.

In another embodiment, the method comprises mixing the metal oxide semiconductor nanomaterial or the metal oxide semiconductor nanomaterial surface coated or adhered with the hemostatic polymer into a topical cream and then applying the topical cream to a subject to an infected area on the subject. With such low toxicity, the topical cream would provide antimicrobial properties, antibacterial properties, antifungal properties, or combinations to the subject and eliminating the microbe, bacterium, or the fungus.

In still another aspect, the method comprises adding the metal oxide semiconductor nanomaterial or the metal oxide semiconductor nanomaterial surface coated or adhered with the hemostatic polymer to a hydrophobic coating. The method comprises mixing the metal oxide semiconductor nanomaterial or the metal oxide semiconductor nanomaterial surface coated or adhered with the hemostatic polymer with a hydrophobic coating. After applying this coating to an article, the coating would provide water repellency and antimicrobial properties, antibacterial properties, antifungal properties, or combinations to the article. Non-limiting examples of these articles may be metals, glass, and ceramics used in many applications.

In yet another embodiment, the metal oxide semiconductor nanomaterial may be used in photovoltaic cells. The method comprises adding the metal oxide semiconductor nanomaterial into the photovoltaic cell. With such a narrow bandgap, previously described above, photons from light would be absorbed by the metal oxide semiconductor nanomaterial thereby generating free electrons and electricity.

In still another embodiment, the metal oxide semiconductor nanomaterial or the metal oxide semiconductor nanomaterial surface coated or adhered with the hemostatic polymer may be incorporated into various coatings such as paints and epoxy resins. After application and drying of the paints or epoxy resins, the coating would provide antimicrobial properties, antibacterial properties, antifungal properties, or a combination thereof. These coatings would be useful in a number of areas such as a hospital, a clinic, food industry, plastic, paints, pharmaceutical industry, or cosmetics industry.

The metal oxide semiconductor nanomaterial may be used for chemical catalysis in electrochemical or organic reactions due to its huge surface area and non-homogenous electrical conduction.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1: Preparation of the $(CuO)1-x/(ZnO)x$ Nanomaterial

Into a 20 L reactor equipped with mechanical stirring was added 200 g $Cu(OAc)_2$ and 12 L deionized water (DI). To this solution was added 110 g $Zn(OAc)_2$ and 5 g PEG 4000. This mixture was stirred until add the solids dissolved. Into a 5 L reactor was added 240 g $NH_4HCO_3$ in 3 L DI water. This mixture was stirred until the solids dissolved. Once the $NH_4HCO_3$ solution becomes homogeneous, the $NH_4HCO_3$ solution is slowly added into the 20 L reactor maintaining the mechanical stirring at 200 rpm. Foam begins to form. At this time, 30 mL EtOH is added while the addition of the $NH_4HCO_3$ solution continues. After the addition of the $NH_4HCO_3$ solution is complete, the reaction is stirred for an additional 30 minutes where a solid if formed. The solid is filtered using vacuum filtration. The solid was removed, resuspended in 800 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid is annealed for 20 minutes under a flow of nitrogen yielding 120 g of the nanomaterial.

Example 2: Preparation of the $(CuO)1-x/(ZnO)x$ Nanomaterial at 0.15M (CuO) when x=0

Into a 2 L reactor equipped with mechanical stirring was added 45 g $Cu(OAc)_2$ and 1.2 L deionized water (DI). To this solution was added 0.5 PEG 4000. This mixture was stirred until add the solids dissolved. Into a 500 mL reactor was added 24 g $NH_4HCO_3$ in 0.3 L DI water. This mixture was stirred until the solids dissolved. Once the $NH_4HCO_3$ solution becomes homogeneous, the $NH_4HCO_3$ solution is slowly added into the 2 L reactor maintaining the mechanical stirring at 200 rpm. Foam begins to form. At this time, 3 mL EtOH is added while the addition of the $NH_4HCO_3$ solution continues. After the addition of the $NH_4HCO_3$ solution is complete, the reaction is stirred for an additional 30 minutes where a solid if formed. The solid is filtered using vacuum filtration. The solid was removed, resuspended in 80 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid was annealed for 20 minutes under a flow of nitrogen yielding 12.0 g of the nanomaterial.

Example 3: Preparation of the $(CuO)1-x/(ZnO)x$ Nanomaterial at 0.15M (ZnO) when X=1

Into a 2 L reactor equipped with mechanical stirring was added 49.4 g $Zn(OAc)_2$ and 1.2 L deionized water (DI). To this solution was added 0.5 g PEG 4000. This mixture was stirred until add the solids dissolved. Into a 500 mL reactor was added 24 g $NH_4HCO_3$ in 0.3 L DI water. This mixture was stirred until the solids dissolved. Once the $NH_4HCO_3$ solution becomes homogeneous, the $NH_4HCO_3$ solution is slowly added into the 2 L reactor maintaining the mechanical stirring at 200 rpm. Foam begins to form. At this time, 3 mL EtOH is added while the addition of the $NH_4HCO_3$ solution continues. After the addition of the $NH_4HCO_3$ solution is complete, the reaction is stirred for an additional 30 minutes where a solid if formed. The solid is filtered using vacuum filtration. The solid was removed, resuspended in 80 mL of EtOH, and then filtered. This step was performed an additional time. The solid was removed and dried in a vacuum oven at 60° C. for 3 hours.

The solid was removed from the vacuum oven and cooled to room temperature. The solid was transferred to flat porcelain crucibles maintaining the height of the solid at 1 cm in height. The crucibles were transferred to a drying oven at atmospheric pressure and the solid was dried at 130° C. for 1 hour. The oven's temperature was increased to 300° C. and the solid was annealed for 20 minutes under a flow of nitrogen yielding 12.0 g of the nanomaterial.

Example 4: Antibacterial Properties of the $(CuO)1-x/(ZnO)x$ Nanomaterial

A 200 ppm stock suspension of each nanomaterial tested (CuO1-x/ZnOx, CuO, ZnO, mix CuO and ZnO, and Zn doped CuO) were prepared by adding 20 mg of particles to 100 mL saline (0.86% NaCl) in a 100 mL volumetric flask. The flask was placed in a sonic bath (Bandelin RK 1028 CH, ultrasonic power 1200 W) and sonicated for 10 minutes.

A bacterial suspension was prepared from cells harvested from a 24 h TSA plate (Tryptic Soya Agar, HiMedia) at 36° C. and suspended in saline. Bacterial concentration in the suspension was measured using a nephelometer (PhoenixSpec, BD) and diluted to $10^6$ cfu/mL.

Suspensions in saline of 20 ml nanoparticles and 10 ml of 106 cfu/mL bacteria were mixed to a final volume of 10 mL, in a 50 mL sterile polypropylene test-tube. The tube was incubated and shaken at a known temperature (24° C./36° C.) for 1 hour. At the end of incubation, a volume of 1 mL was taken from the tube and used for preparation of serial dilutions. 1 mL samples from each dilution were plated with molten TSA using the pour plate method. Plates were incubated at 36° C. for 1 and 24 hours and counted. Giving a killing about 99.99% for NED after 1 h.

Example 5: Preparation of Chitosan Coated $Cu_{1-x}O/ZnO_x$ Nanocomposite

This process is conducted in two steps. In the first step, a water-soluble modified chitosan was prepared. The simplest modification is through synthesis of chitosan mesylate salt or chitosan chloride. Suspend chitosan (1 g) in water (80 ml) at ~10° C. To this, add methane sulfonic acid or HCl (~1 mL) dropwise until the solution becomes clear and stir for an additional hour. Resulting modified chitosan was purified by 48 h dialysis against deionized water.

In the second step, modified chitosan was coated over the nanocomposite. To a suspension of Cu1-xO/ZnOx nanocomposite in deionized water (7.5 g/L), add an aqueous solution of the modified chitosan (2.25 g/L) under stirring. The solution was stirred for 8 h at room temperature. Excess/unbound polymer was removed by centrifugation and the slurry was dried under vacuum to obtain chitosan coated Cu1-xO/ZnOx Nanocomposite Example 6: Preparation of Calcium Alginate Coated on $Cu_{1-x}O/ZnO_x$ Nanocomposite To a suspension of nanocomposite in deionized water (7.5 g/L) was added an aqueous solution of Na-Alginate (2.25 g/L) dropwise under stirring. Solution was stirred for 8 h at room temperature. Excess/unbound polymer was removed by centrifugation to obtain Na-Alginate coated nanoparticle slurry. To prepare Ca-Alginate coated nanoparticles, an ion exchange reaction was performed. To the suspension of Na-alginate coated nanoparticles, aq. $CaCl_2$ (10 g/L) was added dropwise and stirred for 3 h. Excess $CaCl_2$ was removed by centrifugation to get Ca-Alginate coated nanoparticles slurry.

What is claimed is:

1. A metal oxide semiconductor nanomaterial composition consisting of a CuO and ZnO nanomaterial in a modified tenorite crystalline structure and at least one hemostatic polymer wherein the nanomaterial consists of clusters of CuO and ZnO quantum dots consisting of unions of heterojunctions consisting of n-type metal oxide nanoparticles and p-type metal oxide nanoparticles; wherein the hemostatic polymer is adhered or coated on the metal oxide semiconductor nanomaterial; wherein the heterojunctions exhibit an anisotropic conduction of electrons and unequal band gaps; and wherein the nanomaterial exhibits a chemical formula of $Cu_{1-x}O/ZnO_x$; wherein x is the atomic ratio of the zinc oxide impurities on the nanomaterial, wherein x is 0.2, and further wherein there is an inhomogeneous distribution of the metal oxide in the surface region of the metal oxide semiconductor nanomaterial.

2. The metal oxide semiconductor nanomaterial of claim 1, wherein the metal oxide semiconductor nanomaterial consists of two regions, where one region is a surface region and the second region is a core region, and the surface region comprises more than 25% by weight of the ZnO and less than 75% by weight of CuO; and the core region comprises less than 10% by weight of the ZnO and more than 90% by weight of the CuO.

3. The metal oxide semiconductor nanomaterial composition of claim 1, wherein the hemostatic polymer consists of chitosan, alginate, gelatin, carboxymethyl cellulose, polyethylene glycol, and combinations thereof.

4. The metal oxide semiconductor nanomaterial composition of claim 1, wherein the hemostatic polymer is from about 1 wt % to about 5 wt % of the metal oxide semiconductor nanomaterial.

5. The metal oxide semiconductor nanomaterial composition of claim 1, wherein the thickness of the hemostatic polymer ranges from about 1.0 nm to about 10.0 nm.

6. The metal oxide semiconductor nanomaterial composition of claim 1, wherein the composition exhibits antimicrobial properties, antibacterial properties, antifungal properties, hemostatic properties, and combinations thereof.

7. The metal oxide semiconductor nanomaterial composition of claim 1, the nanomaterial composition comprising an optical band gap that ranges from 1.2 eV to 2.1 eV.

8. The metal oxide semiconductor nanomaterial composition of claim 7, wherein the optical band gap ranges from 1.74 eV to 1.85 eV.

9. The metal oxide semiconductor nanomaterial composition of claim 8, wherein the optical band gap is 1.8 eV.

* * * * *